US00PP16821P2

(12) United States Plant Patent
Schreurs

(10) Patent No.: US PP16,821 P2
(45) Date of Patent: Jul. 18, 2006

(54) HYBRID TEA ROSE PLANT NAMED 'SCHRAWATT'

(50) Latin Name: *Rosa hybrida*
Varietal Denomination: Schrawatt

(75) Inventor: Petrus Nicolaas Johannes Schreurs, De Kwakel (NL)

(73) Assignee: Piet Schreurs Holding B.V., de Kwakel (NL)

( * ) Notice: Subject to any disclaimer, the term of this patent is extended or adjusted under 35 U.S.C. 154(b) by 73 days.

(21) Appl. No.: 10/112,027

(22) Filed: Mar. 29, 2002

(51) Int. Cl.
*A01H 5/00* (2006.01)

(52) U.S. Cl. ..... Plt./132

(58) Field of Classification Search ..... Plt./130, Plt./131, 132, 141, 142, 143
See application file for complete search history.

(56) References Cited

PUBLICATIONS

Copy of CO PBR A01577, published Sep. 28, 2002.*
Copy of EC PBR 274–01, dated Sep. 28, 2001.*

* cited by examiner

*Primary Examiner*—Howard J. Locker
(74) *Attorney, Agent, or Firm*—C. A. Whealy

(57) ABSTRACT

A new and distinct Hybrid Tea Rose plant named 'Schrawatt', characterized by its glossy dark green leaves; freely branching habit; dark pink and white bi-colored flowers that are arranged in sprays; and good postproduction longevity.

1 Drawing Sheet

Botanical classification/cultivar designation: *Rosa hybrida* cultivar Schrawatt.

BACKGROUND OF THE INVENTION

The present invention relates to a new and distinct cultivar of Hybrid Tea Rose plant, botanically known as *Rosa hybrida*, commercially produced as a cut flower, and hereinafter referred to by the name 'Schrawatt'.

The new cultivar is a product of a planned breeding program conducted by the Inventor in De Kwakel, The Netherlands. The objective of the breeding program was to develop new spray-type cut Rose cultivars with attractive flower petal colors, long and strong stems, and good postproduction longevity.

The new cultivar originated from a cross-pollination made by the Inventor in 1998 of two unidentified proprietary selections, not patented. The cultivar Schrawatt was discovered and selected by the Inventor as a flowering plant within the progeny of the stated cross-pollination in a controlled environment in De Kwakel, The Netherlands.

Since 1999, asexual reproduction of the new cultivar by cuttings in De Kwakel, The Netherlands has shown that the unique features of the new cultivar are stable and reproduced true to type in successive generations of asexual reproduction.

SUMMARY OF THE INVENTION

The following traits have been repeatedly observed and are determined to be the unique characteristics of 'Schrawatt'. These characteristics in combination distinguish the new Hybrid Tea Rose as a new and distinct cultivar:

1. Glossy dark green leaves.
2. Freely branching habit.

3. Dark pink and white bi-colored flowers that are arranged in sprays.
4. Good postproduction longevity.

Plants of the Hybrid Tea Rose differ primarily from plants of the parent selections in flower color.

Plants of the Hybrid Tea Rose can be compared to plants of the cultivar Schovian, disclosed in U.S. Plant Pat. No. 9,629. In side-by-side comparisons conducted in De Kwakel, The Netherlands, plants of the new cultivar differed from plants of the cultivar Schovian in the following characteristics:

1. Plants of the new Hybrid Tea Rose were more freely branching than plants of the cultivar Schovian.
2. Plants of the new Hybrid Tea Rose have smaller flowers than plants of the cultivar Schovian.
3. Plants of the new Hybrid Tea Rose have white and dark pink-colored flower petals whereas plants of the cultivar Schovian have white-colored flower petals.

Plants of the new Hybrid Tea Rose have not been observed under all possible environmental conditions. The phenotype may vary significantly with variations in environment such as temperature and light intensity without, however, any variance in genotype.

BRIEF DESCRIPTION OF PHOTOGRAPH

The accompanying colored photograph illustrates the new Hybrid Tea Rose plant, showing the colors as true as it is reasonably possible to obtain in colored reproductions of this type. Colors in the photograph may differ slightly from the color values cited in the detailed botanical description which accurately describe the colors of the new Hybrid Tea Rose. The photograph comprises a top perspective view of a typical flowering stem of the new Hybrid Tea Rose.

DETAILED BOTANICAL DESCRIPTION

The aforementioned photograph and following observations and measurements describe cut flowering stems of plants grown in De Kwakel, The Netherlands, in a glass-covered greenhouse with day and night temperatures about 19 and 15° C., respectively. Flowering stems used in the photograph and the description were about five months old and had been pruned. In the following description, color references are made to The Royal Horticultural Society Colour Chart, 1995 Edition, except where general terms of ordinary dictionary significance are used.

Botanical classification: *Rosa hybrida* cultivar Schrawatt.

Commercial classification: Hybrid Tea Rose used as a cut flower.

Parentage:

*Female, or seed, parent.*—Unidentified *Rosa hybrida* proprietary selection, not patented.

*Male, or pollen, parent.*—Unidentified *Rosa hybrida* proprietary selection, not patented.

Propagation:

*Type.*—By cuttings grafted onto rootstocks. Typically the *Rosa canina* cultivar Inermis, not patented, is used as the rootstock.

Plant description:

*Form/growth habit.*—Upright and somewhat outwardly spreading; vigorous.

*Productivity.*—In The Netherlands and at a planting density of seven plants per square meter, productivity is about 139 to 150 flowering stems per square meter per year.

*Plant height.*—About 87.5 cm.

*Plant diameter or spread.*—About 105 cm.

*Lateral branches (flowering stems).*—Quantity per pruned plant: Freely branching, about ten. Lateral branch length: About 65 cm. Lateral banch diameter: About 6 mm. Internode length: About 4 cm. Texture: Smooth, glabrous. Strength: Strong. Aspect: Erect. Color: 137D. Thorns: None observed.

*Foliage description.*—Arrangement: Alternate; compound with about three, five or seven leaflets per leaf. Quantity of leaves per lateral branch: About 19. Leaf length (seven-leaflet leaf): About 7 to 18 cm. Leaf width (seven-leaflet leaf): About 7 to 10 cm. Terminal leaflet length: About 5.5 cm. Termnal leaflet width: About 4 cm. Lateral leaflet length: About 3.5 cm. Terminal leaflet width: About 3 cm. Leaflet shape: Ovate. Leaflet apex: Acuminate. Leaflet base: Obtuse. Leaflet margin: Serrulate. Leaflet texture, upper and lower surfaces: Smooth, leathery, glabrous. Leaflet venation pattern: Pinnate. Leaf petiole length: About 3.25 cm. Leaf petiole diameter: About 2 mm. Leaflet petiole length: About 3 cm. Leaflet petiole diameter: About 1 mm. Stipules: Quantity: Two at base of petiole. Length: About 2.2 cm. Width: About 1.1 cm. Texture, upper and lower surfaces: Smooth, leathery, glabrous. Color: Young foliage, upper surface: 137A. Young foliage, lower surface: 137C. Fully expanded foliage, upper surface: 139A. Fully expanded foliage, lower surface: 147B. Venation, upper surface: 147B. Venation, lower surface: 147C. Leaf and leaflet petiole, upper and lower surfaces: 147C. Stipules, upper surface: 137A. Stipules, lower surface: 137D.

Flower description:

*Flower type and habit.*—Consistently symmetrical double flowers; petals arranged in rosettes. Flowers arranged in terminal sprays. Petals not persistent; receptacles persistent.

*Flowering season/time to flower.*—Year-round under greenhouse conditions.

*Spray height.*—About 10 to 30 cm.

*Spray diameter.*—About 10 to 20 cm.

*Quantity of flowers per spray.*—About 4 to 22.

*Flower diameter, fully opened.*—About 5 cm.

*Flower depth (height), fully opened.*—About 1.75 cm.

*Flower longevity as a cut flower.*—About two weeks.

*Flower longevity on the plant.*—About three weeks.

*Fragrance.*—Sweet, typical of *Rosa.*

*Flower buds.*—Shape: Ovoid. Length: About 1.9 cm. Diameter: About 1 cm. Color: 145C.

*Petals.*—Quantity per flower: About 25. Length: About 1.8 to 2.3 cm. Width: About 1.7 to 2.9 cm. Shape: Obovate. Apex: Rounded. Margin: Entire. Texture, upper and lower surfaces: Smooth, glabrous, satiny. Aspect: Initially upright and reflexing with development. Color: When opening, upper surface: 155A; towards margin, 63A. When opening, lower surface: 155B; towards margin, 63B. Fully opened, upper surface: 155A; towards margin, 62A; with subsequent development, dark pink margin fading to 62C. Fully opened, lower surface: 155B; towards margin, 62A.

*Sepals.*—Quantity per flower: About five. Length: About 2.5 cm. Width: About 7 mm. Shape: Lanceolate. Apex: Elongated, apiculate. Base: Cuneate; fused at receptacle. Margin: Ciliate. Texture, upper and lower surfaces: Satiny; pubescent. Color, upper surface: 138B. Color, lower surface: 144A.

*Pedicels.*—Length: About 7 cm. Diameter: About 2 mm. Texture: Smooth; glabrous. Strength: Strong. Aspect: Erect. Color: 146A.

*Reproductive organs.*—Stamens: Quantity per flower: About 130. Anther length: About 2 mm. Anther diameter: About 1 mm. Anther shape: Elliptic. Anther color: 21B. Filament color: 4C. Pollen: None observed. Pistils: Quantity per flower: About 50. Pistil length: About 4 mm. Style length: About 3mm. Style color: 2D. Stigma shape: Bi-lobed. Stigma color: 1C. Receptacle height: About 7 mm. Receptacle diameter: About 6 mm. Receptacle color: 146A.

*Seed/fruit.*—None observed.

Disease/pest resistance: Plants of the new Hybrid Tea Rose have not been observed to be resistant to pathogens and pests common to *Rosa.*

It is claimed:

1. A new and distinct Hybrid Tea Rose plant named 'Schrawatt', as illustrated and described.

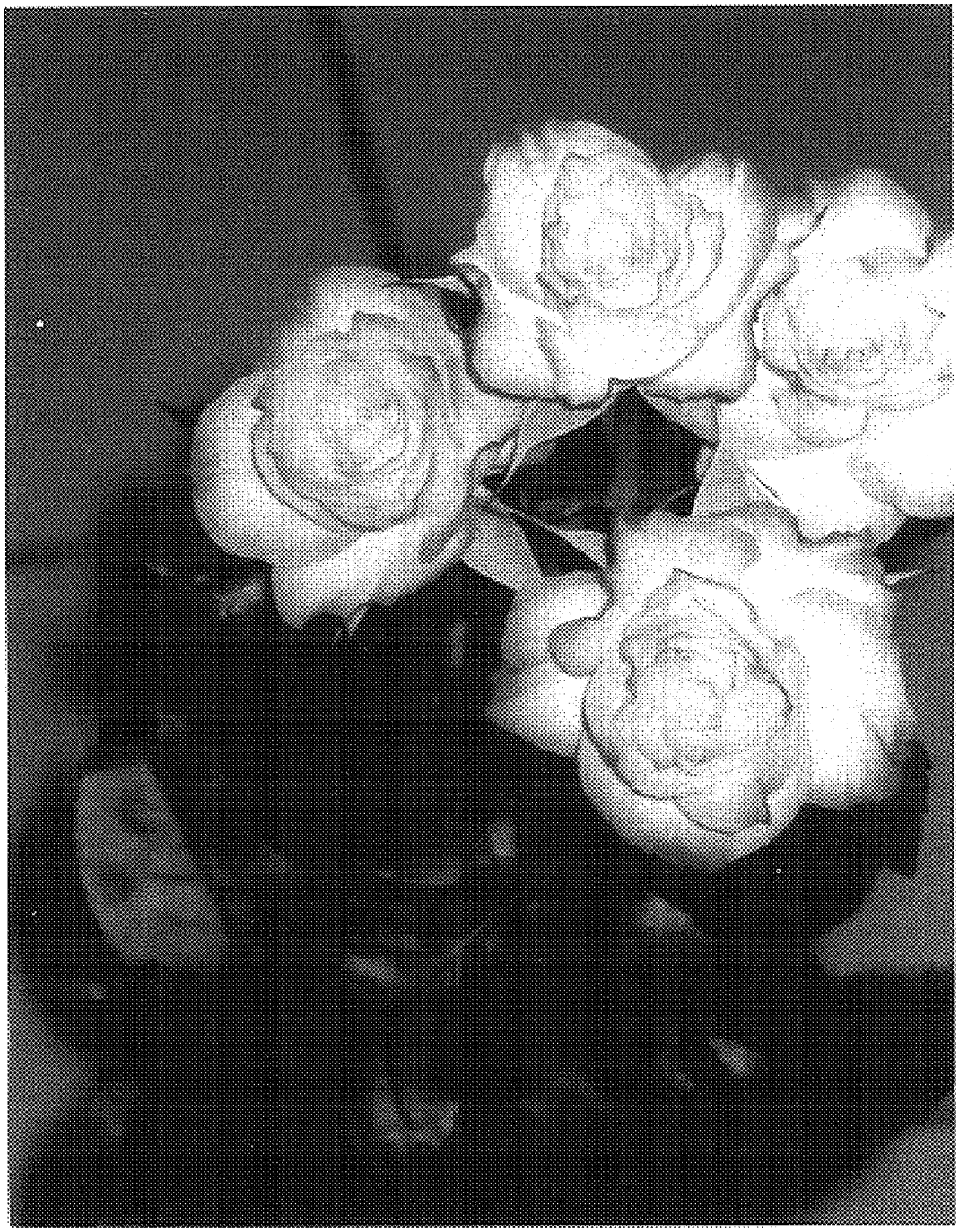

* * * * *